（12) United States Patent
Lee

(10) Patent No.: US 6,974,573 B2
(45) Date of Patent: Dec. 13, 2005

(54) ANTIBODY PRODUCTION IN FARM ANIMALS

(75) Inventor: Sang He Lee, Leiden (NL)

(73) Assignee: MucoVax Holdings, b.v., Leiden (NL)

( * ) Notice: Subject to any disclaimer, the term of this patent is extended or adjusted under 35 U.S.C. 154(b) by 0 days.

(21) Appl. No.: 09/845,036

(22) Filed: Apr. 27, 2001

(65) Prior Publication Data

US 2002/0110555 A1 Aug. 15, 2002

Related U.S. Application Data

(63) Continuation-in-part of application No. 09/720,535, filed as application No. PCT/NL00/00783 on Jan. 22, 2002.
(60) Provisional application No. 60/162,752, filed on Nov. 1, 1999.

(30) Foreign Application Priority Data

Jul. 27, 2000 (EP) .............................................. 00202709
Jul. 27, 2000 (EP) .............................................. 00202710

(51) Int. Cl.[7] .............................................. A61K 39/00
(52) U.S. Cl. .................................... 424/184.1; 424/535
(58) Field of Search .............................. 424/184.1, 535

(56) References Cited

U.S. PATENT DOCUMENTS

| 3,376,198 A | 4/1968 | Petersen et al. |
| 4,994,942 A | 7/1990 | Brown et al. |
| 5,017,372 A | 5/1991 | Hastings |
| 5,260,057 A | 11/1993 | Cordle et al. |
| 5,773,000 A | 6/1998 | Bostwick et al. |

FOREIGN PATENT DOCUMENTS

| EP | 0074240 A2 | 3/1983 |
| JP | 08092108 | 4/1996 |
| WO | WO 97/02835 A1 | 1/1997 |
| WO | WO 98/54226 A1 | 12/1998 |
| WO | WO 99/33954 A1 | 7/1999 |

OTHER PUBLICATIONS

Moffet et al., Human Physiology, Times Mirror/Mosby College Publishing, 1990, p. 402.*
Bohl et al. "Passive Immunity in Transmittable Gastroenteritis of Swine: Immunoglobulin Characteristics of Antibodies in Milk After Inoculating Virus by Different Routes," Infection and Immunity 7:23–32 (1975).
Corthier et al. " Protection against Experimental Psedomembranus Colitis in Gnotobiotic Mice by Use of Monoclonal Antibodies against *Clostridium difficle* Toxin A," Infection and Immunity 59:1192–1195 (1991).

Gardner et al. "Intramammary Vaccination and Hyper–immunized Colostrum as a Prevention for Scour Caused by an Antibiotic Resistant *E. Coli*," 11:76–77 (1976).
Guidry et al. "Effect of Whole *Staphylococcus aureus* and Mode of Immunization on Bovine Opsonizing Antibodies to Capsule," J Dairy Sci 77:2965–2974 (1994).
Ijaz et al. "Effect of different routes of immunization with bovine rotavirus lactogenic antibody response in mice," Antiviral Research 8:283–298 (1987).
Leung et al. "Treatment with intravenously administered gamma globullin of chronic relapsing colitis induced by *Clostridium difficile* toxin," The J of Pediatrics 118:633–637 (1991).
Lyerly et al. "Passive Immunization of Hamsters against Disease Caused by *Clostridium difficile* by Use of Bovine Immuniglobulin G Concentrate," Infection and Immunity 59:2215–2218 (1991).
Ogura et al. "Allergological study of breast feeding ovalbumin and specific IGG IGM and IGA Antibodies to ovalbumin in human milk," Japanese Journal of Allergology 38:342–351 (1989). Article in Japanese with English abstract.
Saif et al. "Immune response of pregnant cows to bovine rotavirus immunization," Am J Vet Res 45:49–58 (1984).
Saif et al. "Immunoglobulin classes of antibodies in milk of swine after intra nasal exposure to pseudorabies virus or transmissible gastroenteritis virus," Infection and Immunity 16:961–966 (1977).
Tomita et al. "Influence of Route of Vaccine Administration Against Experimental Itramammary Infection Caused by *Escherichia coli*," J Dairy Sci 81:2159–2164 (1998).
Woods "Small Plaque Variant Transmissable Gastroenteritis Virus," JAVMA 173:643–647 (1978).

* cited by examiner

Primary Examiner—Patrick J. Nolan
(74) Attorney, Agent, or Firm—Townsend & Townsend & Crew LLP; Nathan S. Cassell

(57) ABSTRACT

The present invention provides means and methods for obtaining an antibody in a mammary secretion product of a farm-animal comprising administering to said animal at least two compositions, which may be the same or different, comprising an antigen to which said antibody is to be raised, the method comprising administering at least a first of said compositions such that a high mucosal and/or systemic immune response is obtained and wherein at least a second of said compositions is administered to a mammary gland and/or a supramammary lymph node of said animal.

57 Claims, 14 Drawing Sheets

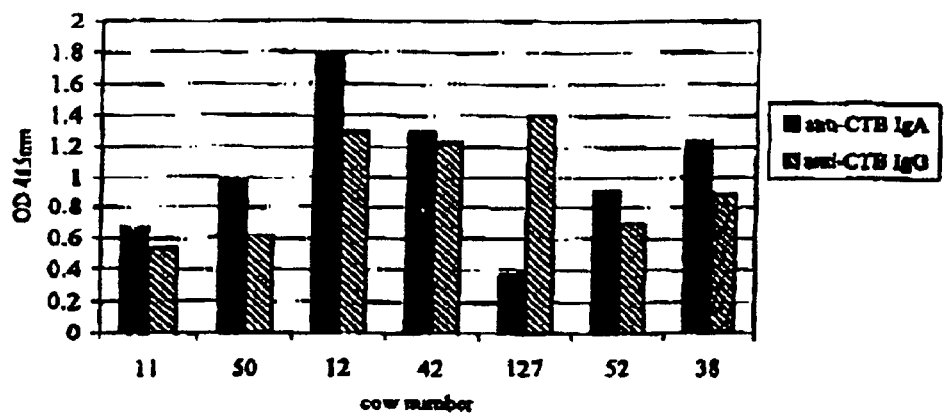
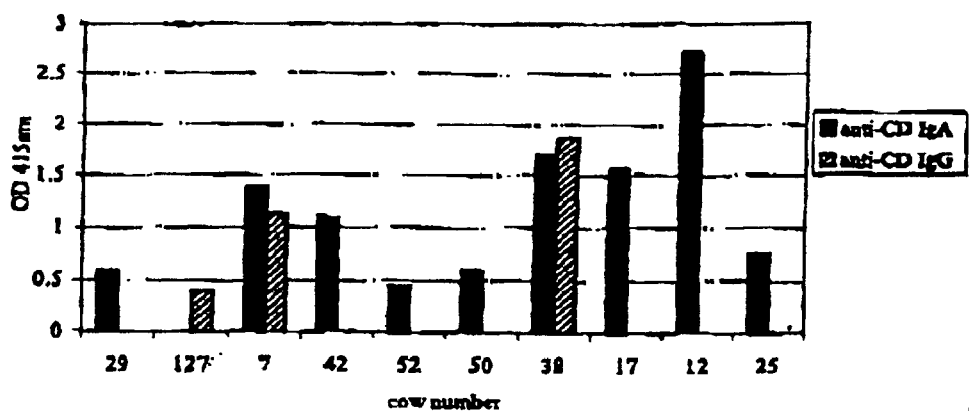

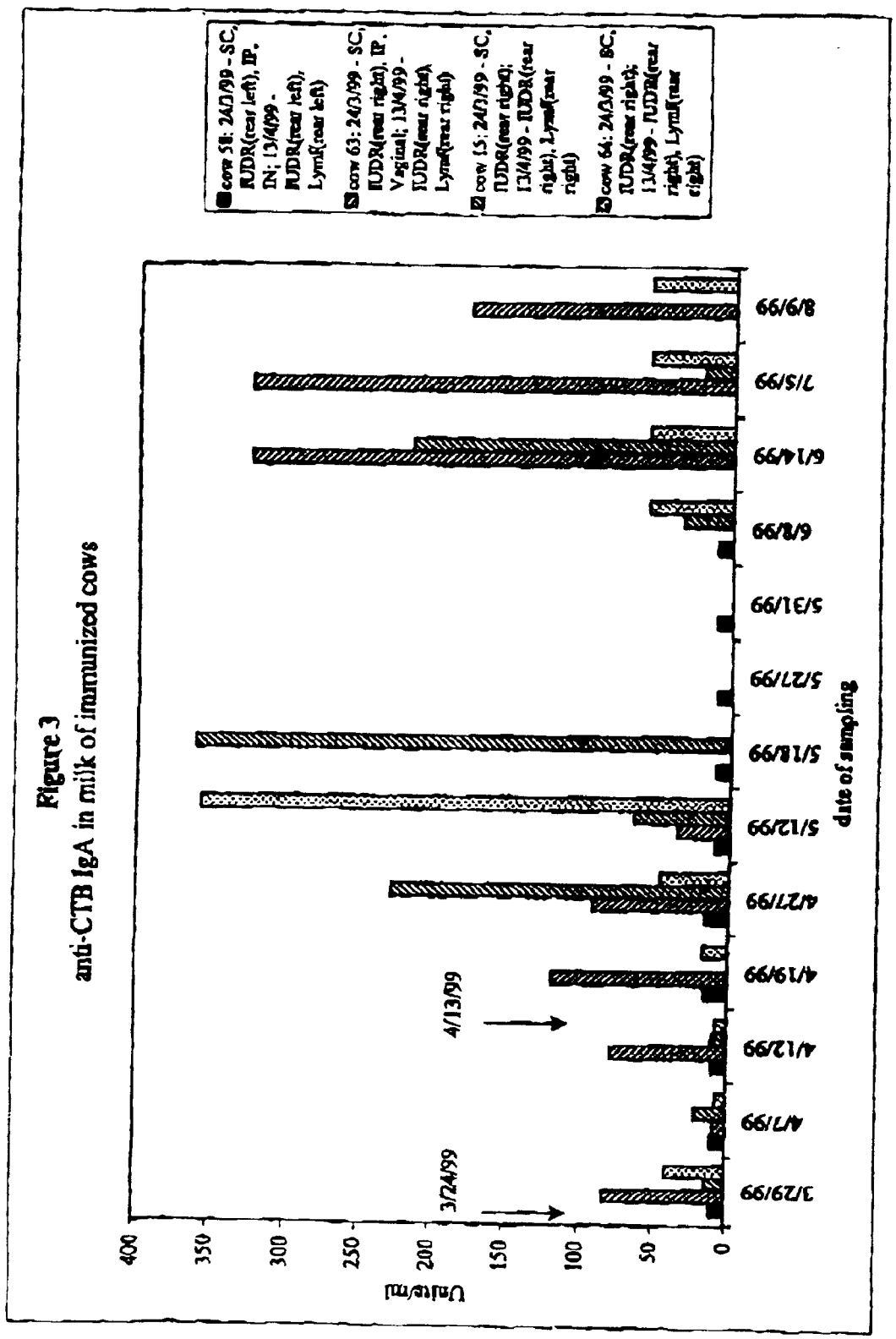

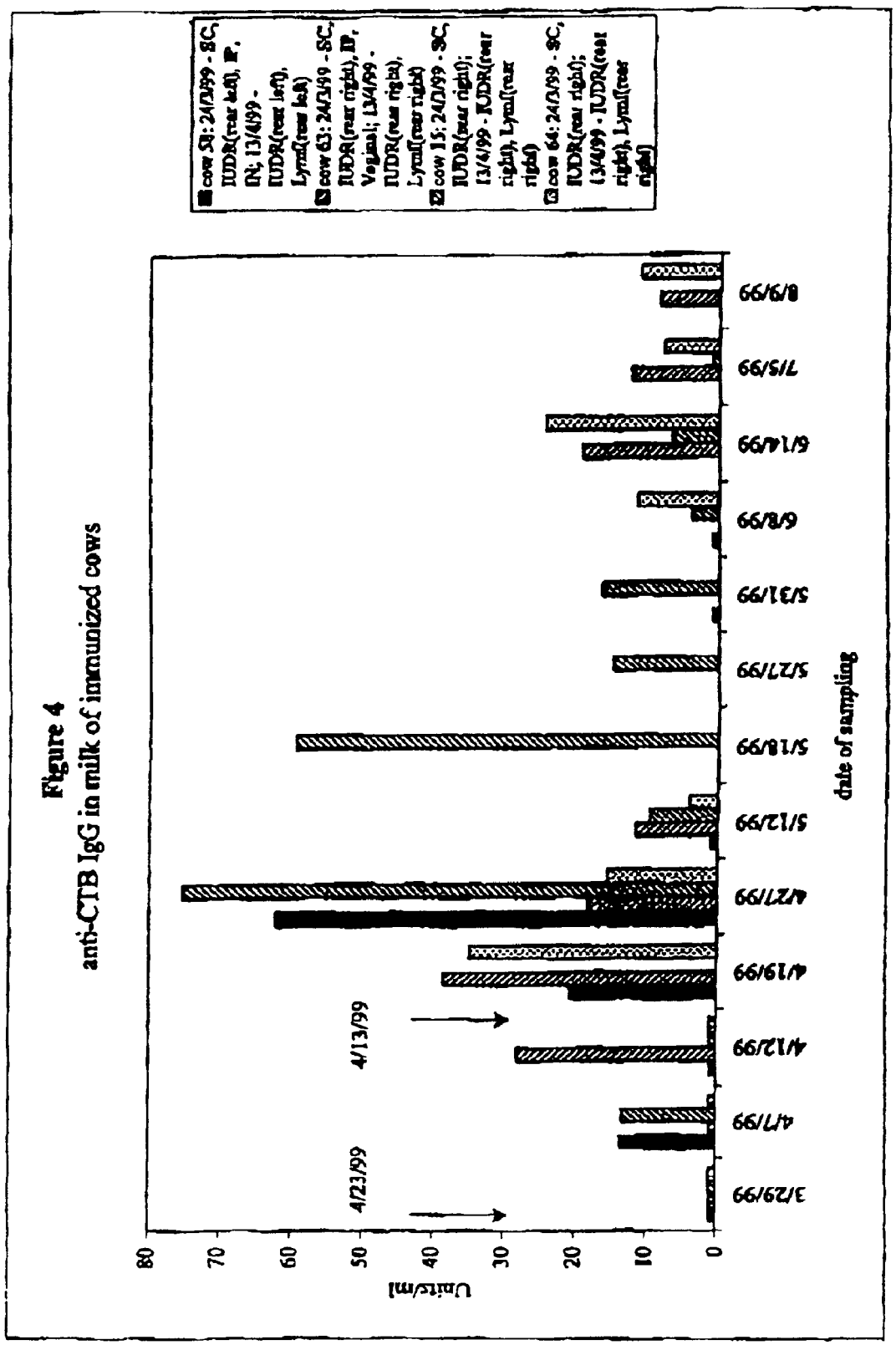

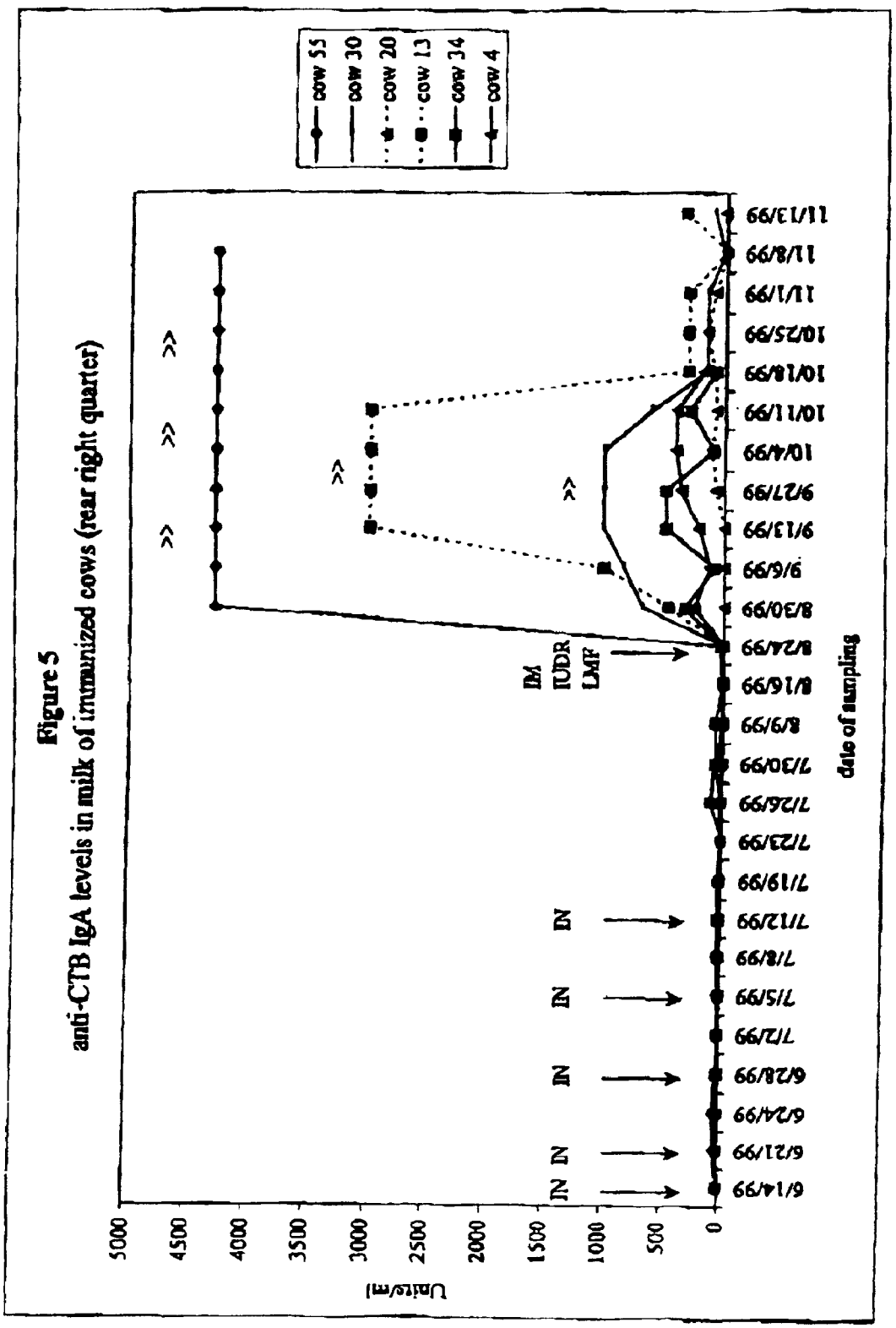

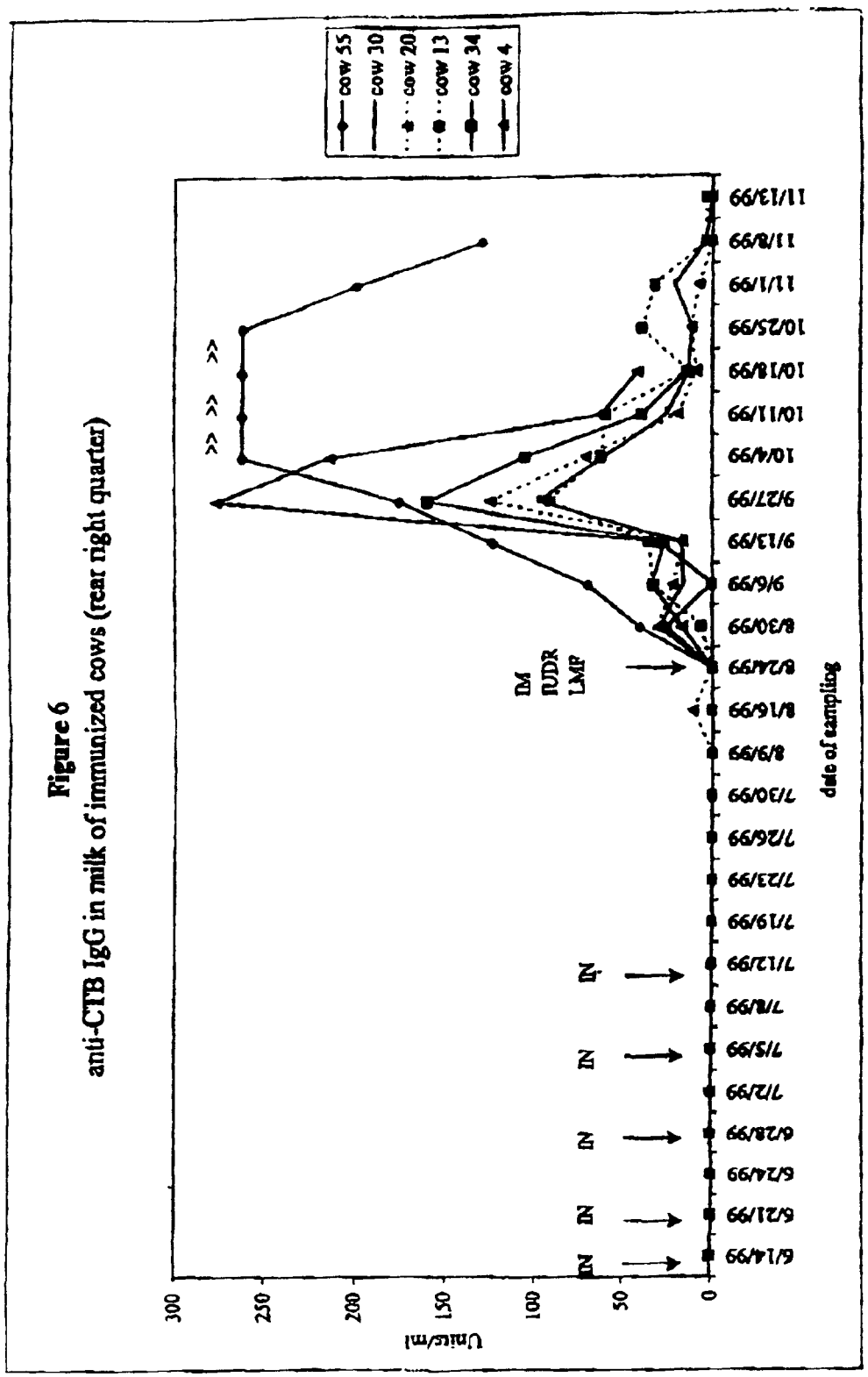

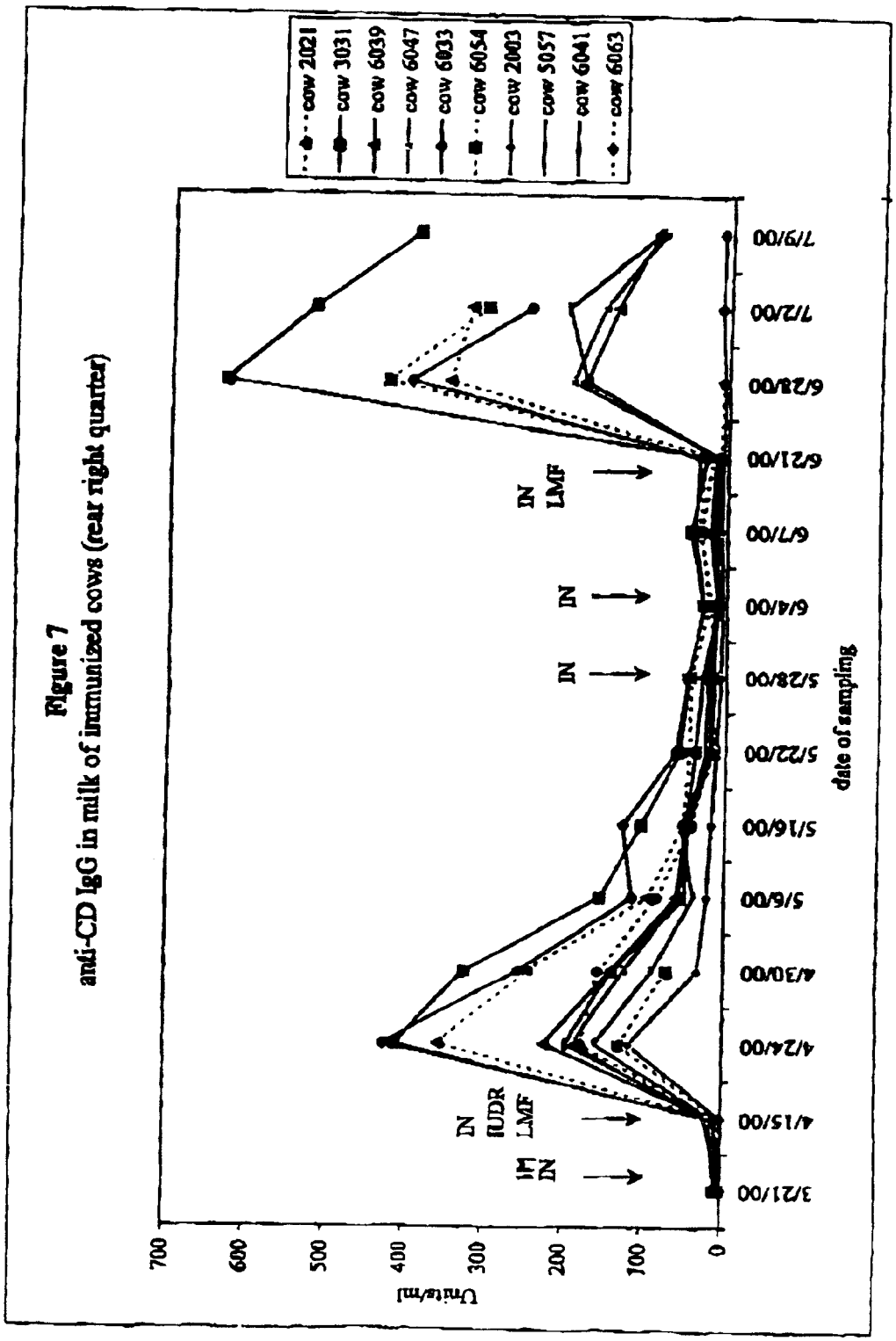

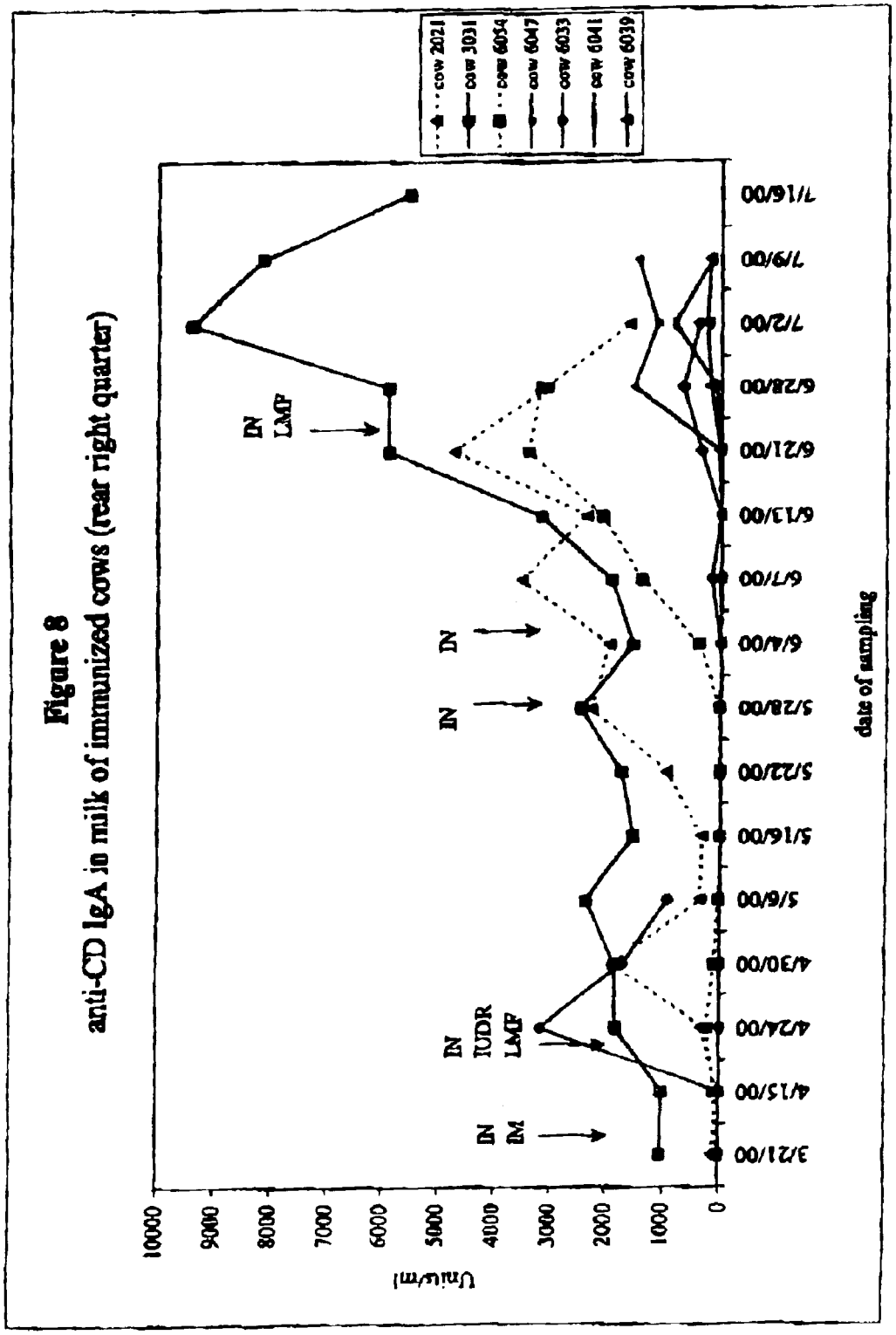

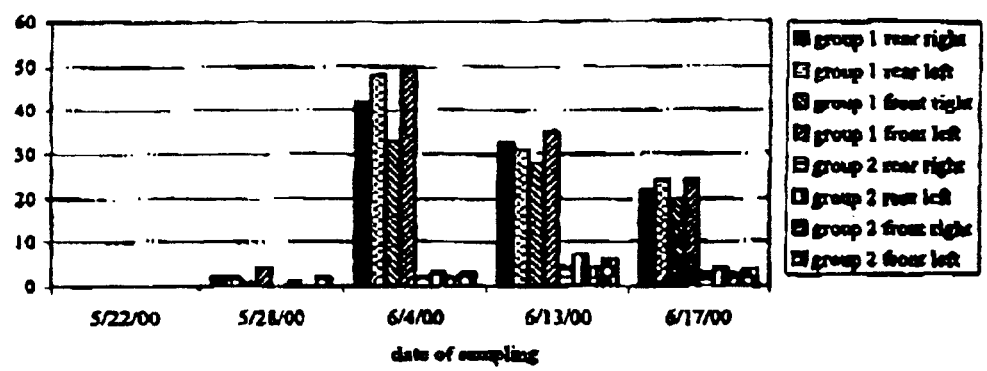
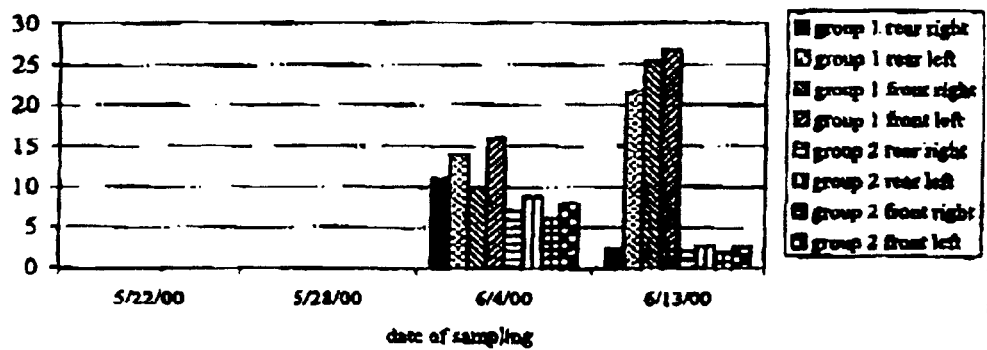

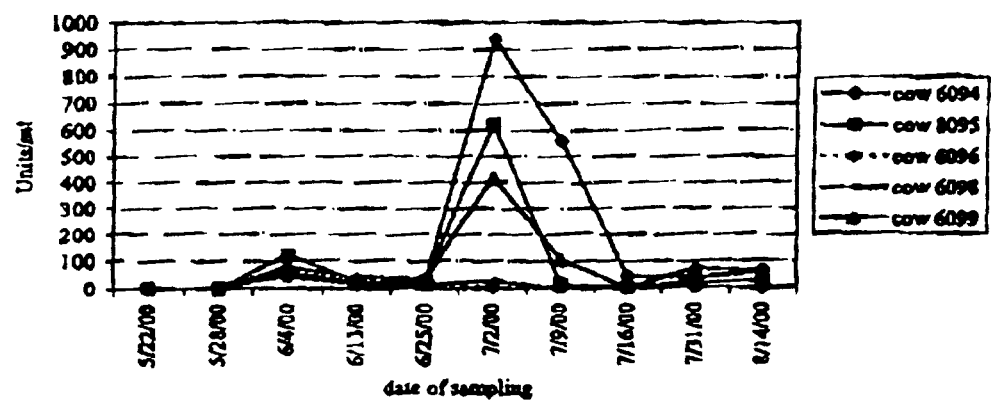
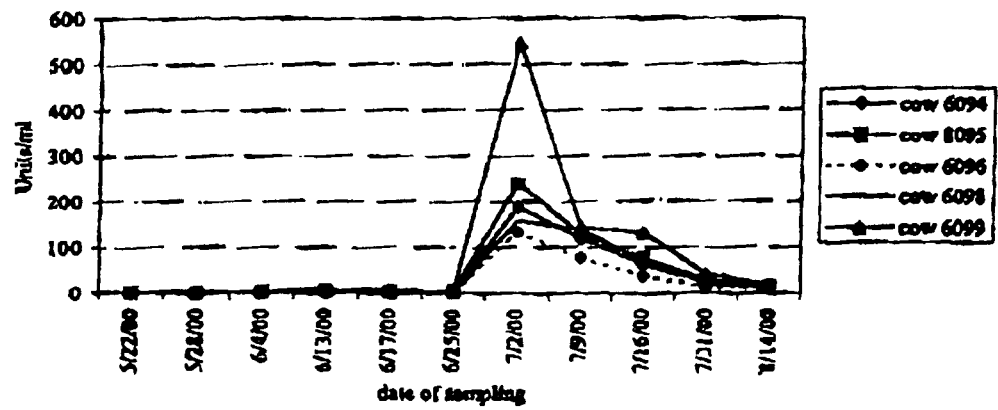

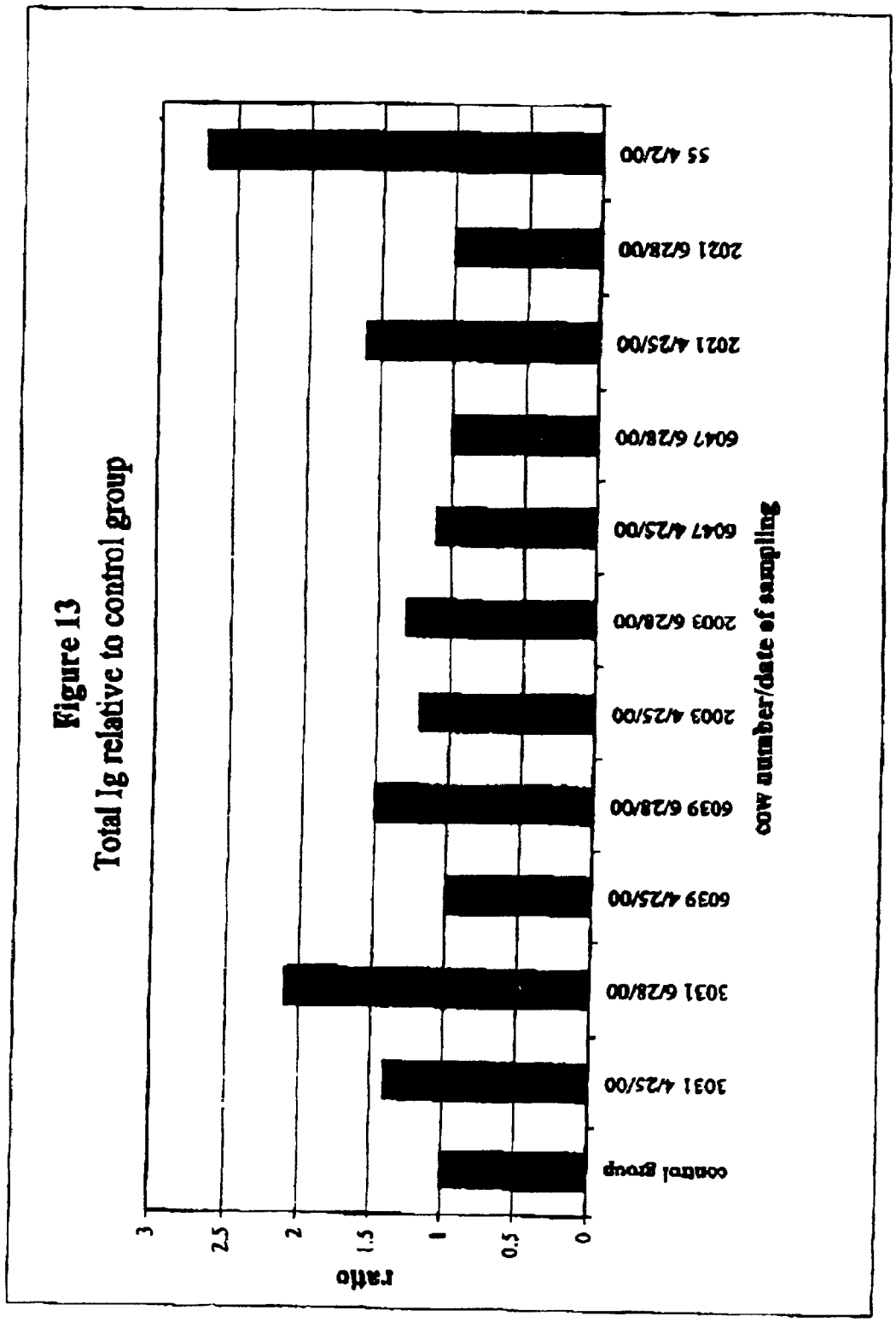

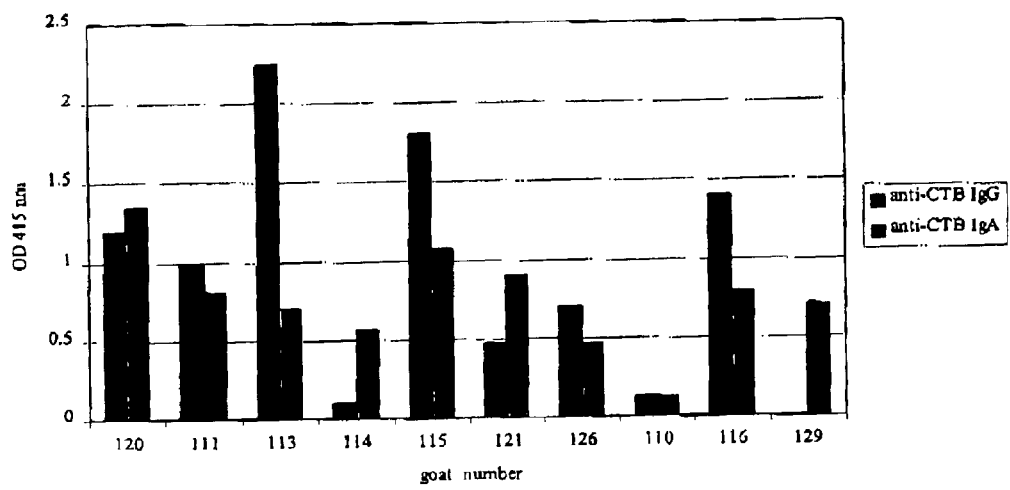
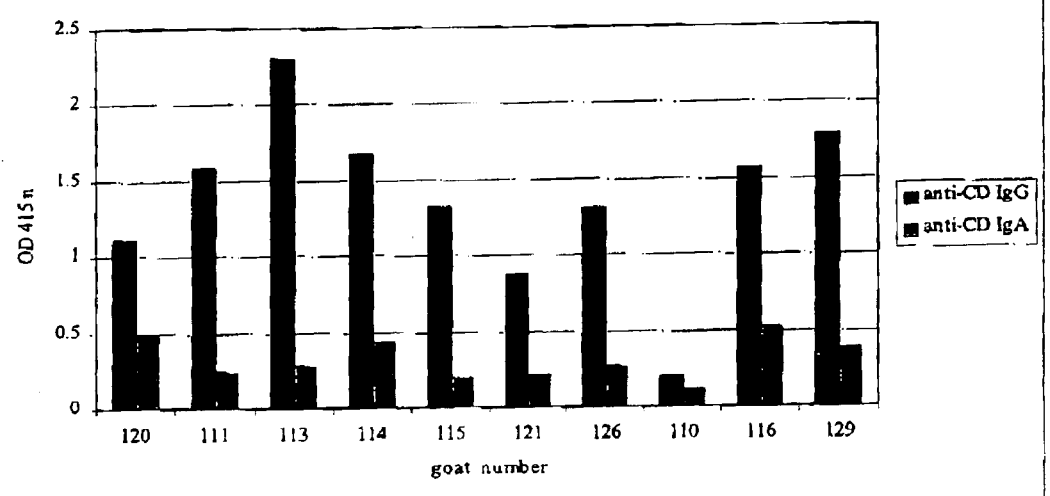

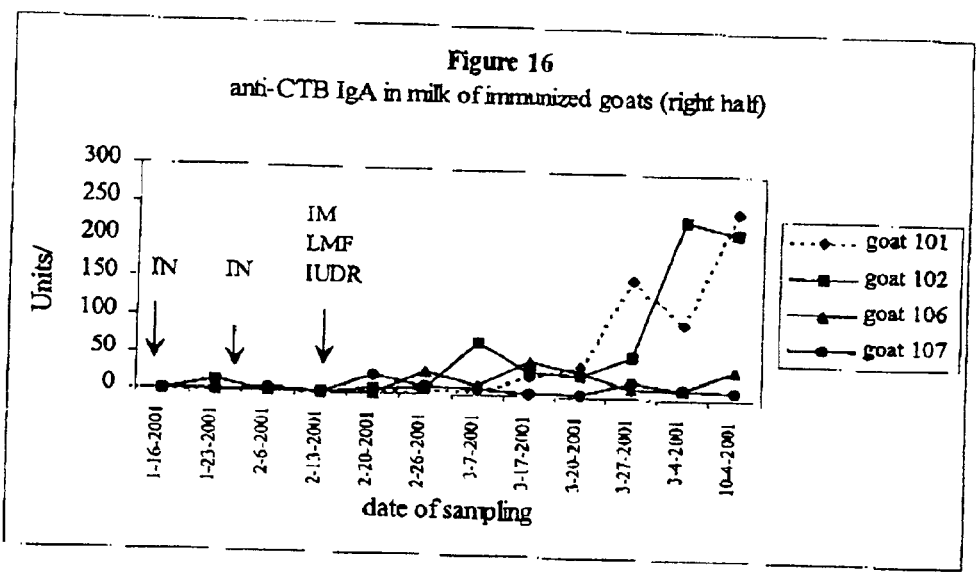

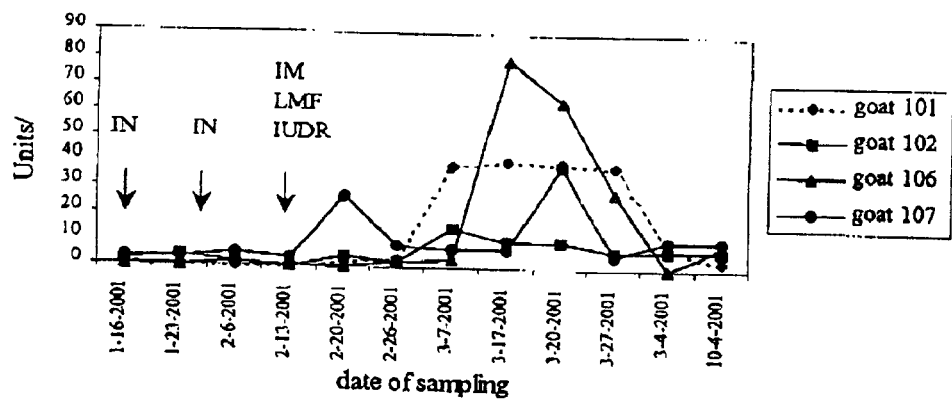
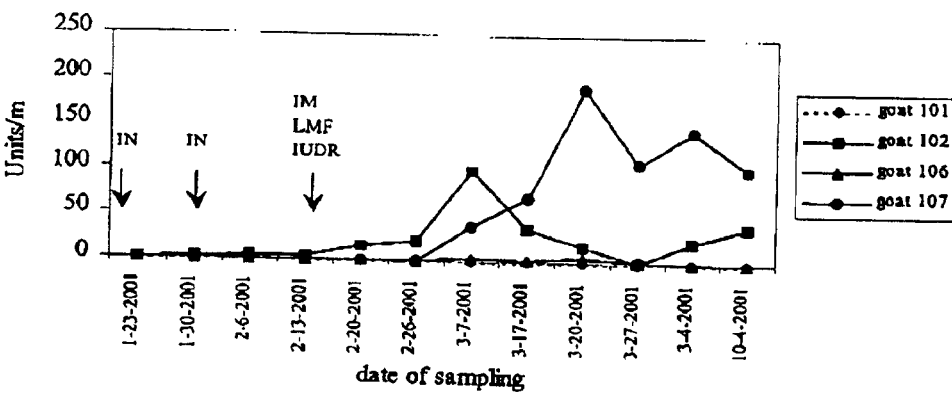

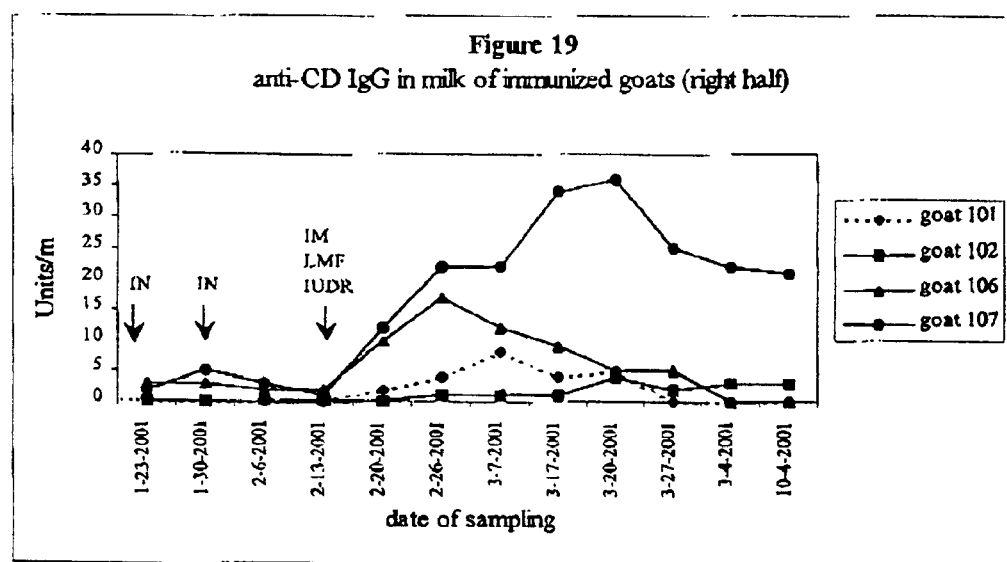

ANTIBODY PRODUCTION IN FARM ANIMALS

This application is a continuation-in-part of 09/720,535, filed Jan. 22, 2002, now pending, which is a 35 USC § 371 application of PCT/NL00/00783, filed Oct. 31, 2000, which claims benefit under 35 USC § 119(e) of provisional application 60/162,752, filed Nov. 1, 1999.

The invention relates to the field of immunology. More in particular the invention relates to means and methods for antibody production.

Antibodies find many applications in science and medicine. They have a remarkable capability to bind to very specific targets, Moreover, it is fairly straightforward to generate new antibodies against a target. Antibodies can be produced in a variety of ways. For most applications antibodies are produced by so-called hybridoma cell lines that result from the fusion of an antibody producing B-cell with an immortalized cell line. Such hybridoma cells can easily be cultured and the antibody can be harvested from the culture supernatant. Another method for the production of antibodies is the harvesting from serum of immunized animals or the production of antibody fragments by bacteria. Of course many other production methods exist Although many different methods for the production of antibodies exist, they all suffer more or less from the same problem. The cost of production is relatively high. For hybridoma based cultured systems, large culture systems need to be set up, validated and maintained. When serum is the source, blood needs to be collected and processed. Moreover, systems need to be in place to check for microbial/viral contamination of the produce. The high production costs prevent the implementation of many applications where the cost of the antibody is important. For instance, many diagnostic kits for diseases are not generally available to third world countries.

One of the routes travelled to reduce the cost of producing antibodies is using farm-animals. Technology for the breeding of farm-animals is widespread and farm-animal housing is relatively cheap. Several initiatives have been undertaken to produce antibodies in the milk of farm-animals. For example, immunization via the supramammary lymph node was described in Guidry et al., J. Dairy Sci. 77(10): 2965–2974 (1994) and in Tomita et al., J Dairy Sci. 81 (8): 2159–2164 (1998). Immunization via either intranasal or intramammary routes was described in Woods, J. Am. Vet. Med. Assoc. 173 (5 Pt 2): 643–647 (1978) and in Bohl et al., Infect. Immun. 11(1): 23–32 (1975). Commercial scale implementation has been attempted by immunization via supramammary lymph node as described in Leitner et al., WO 99/33954 and via direct injection into the mammary tissue as described in Petersen et al., U.S. Pat. No. 3,376,198 and in Hasting, U.S. Pat. No. 5,017,372. However, thus far it is possible to obtain only limited amounts of immunogen-specific antibodies in mammary secretion products of farm animals. Best results are obtained in the colostrum, i.e. the first lacteal fluid that is produced by the female following birth of a young. Milk produced by the female following the colostrial stage is called herein mature milk. Colostrum is quite a unique product that arises from a distinct physiological and functional state of the mammary gland. In ruminants, the principal compositional difference between colostrum and mature milk is the very high content of colostral immunoglobulin, of which IgG class makes up 80–90%.

| Immunoglobulin (mg/ml) | colostrum | Milk |
|---|---|---|
| IgG-total | 32–212 | 0.72 |
| $IgG_1$ | 20–200 | 0.6 |
| $IgG_2$ | 12.0 | 0.12 |
| IgA | 3.5 | 0.13 |
| IgM | 8.7 | 0.04 |

McFadden, T. B. et al. (1997) in Milk Composition, Production and Biotechnology, Welch, R. A. S., Burns, S. R., Popay, A. I. and Prosser, C. G., Eds. pp 133–152, CAB International, New York).

Although the antibody levels in colostrum are higher than in mature (normal) milk, the harvest of the colostrum requires exact timing of the birth since the colostrum only lasts for a maximum of two to three days following birth of the young. Moreover, since colostrum is given only for two or three days, the absolute amounts of antibody that can be collected per animal are limited. For the larger, commercial scale production of antibodies a large collection of farm-animals must be held. The requirement for a large collection of farm-animals also necessitates greater numbers of immunizations etc. thus increasing the logistical problems and production costs. Moreover, due to the thickness/viscosity of the colostrum (it is very thick in fat and protein) the down-stream processing of colostrum is problematic.

For decades, various (immunization) attempts have been made to obtain increased secretion of immunogen-specific antibodies via the mammary gland of farm animals. Such attempts were partially aimed at controlling infections in the mammary gland, i.e, mastitis (Guidry et al., J. Dairy Sci. 77(10): 2965–2974 (1994); Pighetti et al., J. Dairy Sci. 78 (3): 528–537 (1995)) as well as at production of large quantities of immunogen-specific antibodies via milk. The antibody levels in mature milk, however, still remain lower (approximately an order of magnitude) when compared to those that can be achieved in colostrum (Hodgkinson et al., WO 98/54226; Hastings, U.S. Pat. No. 5,017,372). Accordingly, antigen-specific antibodies employed in most clinical and preclinical studies are colostrum-derived and thus belong predominantly to the IgG class (Tollemar et al., Bone Marrow Transpl. 23: 283–290 (1999); Bostwick et al., U.S. Pat. No. 5,773,000; Cordle et al., U.S. Pat. No. 5,260, 057).

The present invention provides a harvested mammary secretion product comprising an antibody specific for an antigen, said mammary secretion product obtainable by a method comprising hyperimmunizing a farm-animal for said antigen and administering said antigen to a mammary gland and/or a supramammary lymph node of said animal and harvesting said mammary secretion product from said farm-animal. Said mammary secretion product surprisingly contains much higher levels of antibody specific for said antigen (herein called antigen-specific antibody) than secretion products obtained via conventional methods in the art. Moreover, it was observed that using the methods of the invention it was possible to obtain substantial amounts of antigen-specific antibody in the mature milk of the lactating animal. Indeed, the levels of such antigen-specific antibodies were in the range of those that can be raised in colostrum. By hyperimmunizing is meant that the animal produces a supranormal level of antigen-specific antibodies in the blood or in mucosal secretion, not in lacteal secretion. A supranormal level means that the amount of antibodies in the animal body is higher than it would be without administration of the antigen, or after a single administration of the antigen. Preferably, said hyperimmunizing comprises administering said antigen to an airway of said animal. With said airway administration it was possible to obtain prolonged production of substantial amounts of antibody in the milk of the animal without necessitating additional booster administrations of said antigen to said animal. However, booster administrations of said antigen to said animal may be performed in cases where the levels of antigen-specific antibody are found to drop after some time. Preferably, said airway administration comprises intra-nasal administration of said antigen. Intra-nasal administration is relatively easy to perform and airway administration has been observed to induce higher levels of antigen-specific antibody in the mammary secretion product and more sustained production of the antibodies in the milk of the animal over time. Preferably, said mammary secretion product is milk. Milk is easy to collect and since the antigen-specific antibody production in the milk is sustained over time it is possible to select a group of animals that have the best levels of antigen-specific antibody in the milk thus improving the overall performance and logistics of the procedure.

The invention thus demonstrates the feasibility of producing a unique lacteal fluid in a prolonged manner. The characteristics of such a fluid are: a) said fluid has the characteristics of colostrum as far as antigen-specific antibody levels are concerned; b) yet the overall compositional characteristics of said fluid are comparable with those of milk. By the characteristics of colostrum as far as antigen-specific antibody levels are concerned is meant herein, that the amount and/or kind of antigen-specific antibody is more comparable to colostrum than to milk. For instance, the amount of antigen-specific antibody in the fluid has to be higher than the amount of antigen-specific antibody normally obtained in milk. In that case the amount of antigen-specific antibody in the fluid is at least in part comparable to the amount of antigen-specific antibody in the colostrum, because both amounts are higher than the amount of antigen-specific antibody normally obtained in milk.

It is clear that any immunization schedule resulting in an animal that is hyperimmunized for said antigen can be combined with administration of antigen to a mammary gland and/or supramammary lymphnode, to obtain the result. There is no real need to assess whether an animal is hyperimmunized before administration of antigen to a mammary gland and/or supramammary lymphnode is done. One can easily determine the antibody level in mammary secretion product of said animal. A low level of antibody in said secretion product indicates that said animal was not hyperimmunized and additional administration of antigen is required to achieve hyperimmunization. A group of animals treated with a method of the invention may contain individuals that do not respond or not respond to a sufficient extend. Such non-responders can be excluded from the collection of milk. With a method of the invention it is possible to obtain at least 25% responders in a group. Frequently at least 50% of the animals treated with a method of the invention respond to exhibit prolonged high antigen-specific antibody production in the milk of a lactating farm-animal and/or mammal.

Antigen to which said antigen-specific antibody is raised can be any compound or collection of compounds capable of eliciting an immune response. Typically said antigen comprises a protein or a functional part, derivative and/or analogue thereof Antigen administered to said animal does typically not differ from administration to administration to the animal. However, this does not necessarily have to be true. It is possible to use different manifestations of antigen, for instance different proteins, as long as different manifestations comprise at least one part that is immunologically the same. By immunologically the same is meant that an antibody is capable of recognizing different manifestations of said antigen. Antigen may also be administered through administering nucleic acid encoding said antigen or functional equivalent thereof to said animal. Administered nucleic acid can be expressed by cells of said animal to which said nucleic acid has been delivered. Expression of said antigen or functional equivalent in cells of the animal leads to the mounting of an immune response. This technology is also in the art referred to as nucleic acid vaccines.

Without being bound by theory it is thought that a high general immune response is required to provide a substantial pool, circulation or reservoir of antigen-specific antibody producing cells. A mammary gland and/or supramammary lymphnode immunization is required to attract cells from the pool, circulation or reservoir to the mammary tissue such that secretion of the antigen-specific antibody to the mammary excretion product is enabled. It is preferred that the generation of the pool, circulation or reservoir is achieved with an immunization schedule resulting in a high mucosal immune response since in this way at least part of the pool, circulation or reservoir may be primed toward the mammary gland. Thus facilitating earlier and more pronounced secretion of the antigen-specific antibody upon mammary gland and/or supramammary lymphnode immunization. Preferably, however, the pool, circulation or reservoir is generated through an immunization schedule resulting in a high mucosal and/or systemic immune response.

An immunization schedule comprises one or more administrations of antigen to a farm-animal. An immunization schedule resulting in a high mucosal and/or systemic immune response is preferably at least in part achieved through inhalation of antigen by said animal. The composition for inhalation is of course preferably administered such that antigen in the composition is distributed throughout the major part of the airway of said animal. Airway administration is preferably achieved in the form of aerosols. Preferably, said airway administration is performed through intra-nasal administration. Preferably the immunization schedule resulting in a high mucosal and/or systemic immune response comprises at least two airway administrations of a composition comprising the antigen. More preferably, it comprises at least four airway administrations of a composition comprising the antigen.

With means and methods of the invention both a mammary gland immunization and a supramammary lymphnode administration of a composition containing the antigen have the effect of enabling the secretion of large amounts of antigen-specific antibody in the milk of a farm-animal. Preferably at least one administration is performed in the supramammary lymphnode Preferably, at least two administrations are performed in the supramammary lymphnode. Supra-mammary lymphnode administration results in a higher and earlier surge of antigen-specific antibodies in the milk.

Means and methods of the invention are suited to obtain high and prolonged antigen-specific antibody production in the milk of any lactating mammal. Preferably, said animal is a farm-animal. Farm animals are animals that are used on a commercial basis by man, be it for the production of milk, meat or even antibodies. Farm-animals already used for the commercial scale production of milk are preferred for the present invention since for these animals special lines and/or breeds exist that are optimized for milk production. Preferably, said farm-animal is a cow or a goat. More preferably said farm-animal is a cow.

Using the methods of the invention it is possible to obtain high levels of antigen-specific antibody in any mammary secretion product such as for instance the colostrum or milk.

Antigen-specific antibodies in the milk can be of any immune class. However, preferably said antibodies are of the IgG and/or IgA class. More preferably, said antibodies are of the IgA class.

Milk, containing antigen-specific antibodies is preferably collected by milking the animal. Milk thus collected can either be used directly, or the milk can be further processed, for instance to purify antigen-specific antibodies. Methods for the (partial) purification of (antigen-specific) antibodies from milk are present in the art and need not be listed here.

Antigen-specific antibodies of the invention can be used for almost any purpose. Preferably said antibodies are used for a purpose that polyclonal antibodies are used for in the art. However, using purification methods in the art it is also possible to obtain essentially monoclonal antibodies, for instance through immunization with an antigen comprising essentially only one immunogenic part. Essentially monoclonal antibodies can also be produced in other ways for instance through immune purification of antibody using a peptide, comprising essentially only one binding region for antibody. Antigen-specific antibodies (purified from the milk or not) are preferably used for the preparation of a medicament. Such antibodies can be used for instance for the preparation of medicaments for the treatment of skin wounds, for instance with an antibody specific for a skin bacterium. Such antibodies are also particularly suited for the treatment of disease that are caused by pathogens in the gastro-intestinal tract. In general, the antigen-specific antibodies from the milk of a farm animal can be used in any (at least in part) immune protected area of the human body. Such areas are for instance the gastro-intestinal tract, the respiratory tract, the urogenital tract, the eye, the mouth and the skin. However, such antibodies can also be used to bind antigens that can be reached by the blood flow in a patient, for instance following systemic administration of the antibodies to said individual. Considering that the individual to be treated is usually a human, and the antibodies are derived from a farm-animal, it is expected that the immune system of the individual will respond to the administered antibodies, especially when administered systemically. However, many applications of such systemic administration of antibodies are still possible. For instance, when the individual has as yet not mounted an immune response to the antibodies (as for instance is the case in a first use in said individual) or when the immune response has faded (over time).

Antigen-specific antibodies (purified from the milk or not) can also be used for the preparation of for instance a food product. Many bacterial but also viral microbes can be present in the gastro-enteric tract. Some of those microbes can be present sub-clinically. With a method of the invention antibodies can be generated that are specific to one or more of said microbes. Such antibodies can be used to prepare a food product or other product. By eating the product, antibodies toward said one or more microbes are released in the gastro-enteric tract thus at least in part preventing said microbes from multiplication.

Considering that the antibodies are produced in a farm-animal, the antibodies will typically be specific for antigens that are not naturally present in said animal (non-self). Thus generally antibodies can be produced against any antigen that is foreign to the animal. Typically such antibodies comprise specificity toward bacteria, viruses and toxins thereof. However, antibodies can also be raised against mammalian antigens when there is sufficient divergence between the antigen administered and the homologue of the antigen in the farm-animal. Although less straightforward it is also possible to generate an antibody response to at least some self-antigens. Several methods to achieve that result exist in the art.

One or more of the immunization schedules may further include administration of one or more other compounds capable of stimulation and/or modulating an immune response of the farm-animal. Suitable adjuvants are known in the art and may include among others Freund's incomplete adjuvant, aluminum hydroxide, saponin/cholestrol based immune-stimulating complexes ISCOMS, and the glyceride-polysorbate based adjuvant 'RhinoVax' (Jakobsen et al. Infect. Immun. 67: 4128–4133 (1999). Preferably, said adjuvant is capable of modulating an immune response toward a mucosal immune response. Non-limiting examples of such compounds are $1\alpha,25(OH)_2D_3$, cholera holo toxin, toxin A and toxin B of *Clostridium difficile*, cytokines such as IL-5, IL-6, IL-12 or TGF-3, unmethylated $C_pG$ (bacterial DNA) sequences with phosphodiester backbone. Commercially available alternatives to Freund's complete adjuvants include Ribi adjuvant system (RAS), Titer Max, Syntex Adjuvant Formulation (SAF), Elvax 40W, Montanide, AdjuPrime, Gerbu Adjuvant and Super Carrier. Antigens can also be coprecipitated with L-tyrosine or absorved to nitrocellulose for slow release. Of course also combinations of adjuvants can be used.

Methods of the invention may be used to elicit an immune response against the antigen in the farm-animal. However, it is of course also possible to use the methods of the invention to amplify an already existing immunity toward the antigen in the farm-animal.

The farm-animal can be immunized against one antigen, however considering that a polyclonal immune response is generated, antigen-specific antibodies in the milk typically comprise specificity toward two or more different parts of the antigen. When antigen is used that comprises a complex mixture of different compounds, many antibodies comprising specificity for different parts of the antigen will be generated and be present in the milk of the animal. It is of course easy to repeat a method of the invention for another antigen one or more times and thus generate mammary secretion product comprising set of antibodies for one or more antigens or several cross-linked antigens.

Immune responsiveness of farm animals to a given antigen can be further enhanced via genetic manipulation to the animals. For example, each of the numerous biochemical steps that are critically involved in the process from B-cell activation to antibody secretion in the mucosal surfaces can be optimized via genetic modification- Non-limiting examples are: increased expression of specific MHCantigen molecules for efficient antigen presentation, increased expression of J-chain for increased IgA dimer formation, and/or increased expression of homing receptors for increased migration of activated lymphocytes to the mammary tissue. Expression of numerous cytokines and lymphokines which are involved in the process can also be manipulated to optimum levels for maximum antibody secretion. Furthermore, animals that are proven to be high responders to a given antigen can be cloned, so that upon immunization of the cloned animals, high antigen-specific antibody yields are ensured.

In one embodiment the antigen comprises a collection of compounds harvested from a culture of *Clostridium difficile*.

This collection of compounds contains several proteins among which formaldehyde-inactivated *C. difficile* (VPI10463) cells, formaldehyde-inactivated spores of said bacterium and formaldehyde-inactivated *C. difficile* toxoids which are toxin A and toxin B. Antibodies raised against this collection will typically comprise specificity toward more than one protein of *C. difficile*. Preferably, said antibodies comprise antibodies specific for spores of *C. difficile*. Preparations of such antibodies can be used for the preparation of a medicament for the treatment of diseases associated with *C. difficile* infections. Administration to an individual is preferably performed such that antibodies are delivered to the gut. Several methods exist in the art to allow for such delivery, for instance, antibodies can be contained in pills that release their content to the gut. In a preferred embodiment of the invention the antibodies of the invention comprise specificity toward spores of the *C. difficile*. Such antibodies are particularly useful to at least in part prevent recurrence of *C. difficile* related disease. Typically, *C. difficile* related disease is treated with medication directed toward removal of bacteria of *C. difficile*. Such medication can consist for instance of the administration of antibiotics and/or antibodies directed toward one or more bacterial components of *C. difficile*. Although this treatment is usually successful in curing the patient from symptoms, it is often (20% of the cases) not sufficient to prevent recurrence of the disease in the patient. Recurrence can at least in part be prevented by delivering to the gut of the patient antibodies with a specificity toward spores of *C. difficile*. Binding of said antibodies to at least part of the *C. difficile* spores in the gut at least in part reduces the propensity with which said spores can hatch. Thus preventing at least in part, recurrence of *C. difficile* related disease in the patient. Thus the invention also provides a composition comprising an antibody capable of binding to a spore of *C. difficile*. Further provided is the use of a *C. difficile* spore specific antibody for the preparation of a medicament. Preferably, said antibody is used for the preparation of a medicament for the treatment of *C. difficile* related disease.

Lactating farm-animals can suffer from bacterial and/or viral infections in the mammary gland. Such infections can at least in part be treated by enabling antigen-specific antibody secretion into the secretion compartment of the mammary gland. One of such diseases is mastitis. The invention therefore further provides a method for the treatment of microbial infection of a mammary gland in an animal comprising administering to said animal an antigen such that a high immune response is obtained and administering said antigen to a mammary gland and/or a supramammary lymph node of said animal, wherein said antigen comprises at least a part of said microbe or a functional derivative and/or analogue thereof. Said immune response may be a systemic immune response. Preferably, said immune response is a general (both systemic and mucosal) immune response. Preferably, said animal is suffering from or at risk of suffering from mastitis.

The invention further provides a use of an antigen for the preparation of a medicament for the treatment of a microbial infection of a mammary gland, wherein said medicament comprises a composition for airway administration of said antigen and a composition for mammary gland and/or supramammarylymphnode administration of said antigen. Preferably, said microbial infection causes mastitis. Said medicament may also be suitable for the treatment of a human.

Mastitis is a disease that causes the transient and sometimes permanent loss of milk production. Loss of milk production can be induced by the disease itself or by the use of antibiotics that affect the milk production, or both. Animals suffering from mastitis get very sick and sometimes die. Mastitis considerably effects the amount of labor and costs of production for a farmer.

In another aspect the invention provides milk obtained from a lactating farm-animal comprising at least 0.5 $\mu$gram/ml antigen-specific antibody. Preferably, said milk comprises at least 15 $\mu$gram/ml antigen-specific antibody. More preferably, said milk comprises at least 50 $\mu$gram/ml of antibody against which said animal has been immunized with a method of the invention.

Administration of antigen to said animal can be achieved through means known in the art. Typically antigen is administered in a range that for a protein of approximately 10 kD varies between 5–500 $\mu$gram. Antigen based on whole (inactivated) cells and/or spores, is typically administered such that the equivalent to the range of $10^8$ and $10^{11}$ cells and/or spores are provided to said animal. Other concentrations and/or amounts can be used as well, depending on the size of the animal, the immunogenicity of the antigen and/or adjuvants and other variables known in the art.

Much evidence exists in the literature that pathogen-specific antibodies obtained from colostrum and milk of cows are effective for prevention and treatment of gastrointestinal infections caused by various pathogens. In spite of promising indications, however, product development has not yet been widely materialized due mainly to unavailability of sufficient amounts of pathogen-specific antibodies, It is relatively easy to obtain high levels of antigen-specific antibodies from colostrum of cows after immunization via conventional methods. However, secretion of colostrum lasts only for 2 to 3 days after each calving and as soon as they enter into a mature lactation period, levels of such antibody drop close to nil. In the present invention, we describe immunization methods that result in secretion of high levels of antigen-specific antibodies not only in colostrum but also in mature milk of lactating farm-animals for a sustained period of time, As we show in the examples, using a method of the invention it is possible to obtain mature milk from an animal, comprising antigen-specific antibody in a quantity which is at least half as much as which is in average possible to obtain in the colostrum of said animal using conventional methods of the art.

Therefore, in one aspect the present invention provides mature milk obtainable from a mammal, comprising an antigen-specific antibody in a quantity of at least 50 percent of the average quantity of said antigen-specific antibody obtainable in colostrum from said mammal, wherein said colostrum is obtained after immunization of said mammal against said antigen. Preferably, said antigen-specific antibody consists of IgA, because IgA forms dimers which are very well capable to form complexes.

By an average quantity of said antigen-specific antibody obtainable in colostrum is meant herein a quantity which is the average of yields of antigen-specific antibody, obtained from colostra from different unselected animals, which have been immunized against said antigen.

A yield of at least 50 percent is an important improvement, because in the prior art only yields of antigen-specific antibody in mature milk of about one tenth compared to yields obtained from colostrum was possible. However, as we show in the examples, the present invention provides higher yields of IgA in mature milk than the yields that were obtained in colostrum using conventional methods of the art. Thus, in a preferred aspect the invention provides mature milk according to the invention, wherein said percentage is at least 100 percent, more preferably at least 200 percent.

EXAMPLES

Materials and Methods

DUKORAL®, an oral cholera vaccine approved for human use, was purchased from SBL Vaccin AB, Stockholm. Each ampule consists of formalin-inactivated *Vibrio cholera* and cholera toxin subunit-B (CTB), at concentrations of $10^{11}$ cells and 1 mg protein, respectively, in 3 ml phosphate-buffered saline, pH 7.4 (PBS).

*Clostridium difficile* whole-cell. *C. difficile* whole-cell was prepared and inactivated as described previously. Briefly, *C. difficile* VPI 10463 was grown in BHI medium at 37° C. under an anaerobic atmosphere for 36 h. Cultures were centrifuged and cells were washed three times with PBS. The resulting pellets were resuspended in PBS containing 1% (vol/vol) formaldehyde and kept at 4° C. until use. Before each immunization, excess formaldehyde was removed by two washes with PBS. Inoculation of the equivalent to $10^9$ *C. difficile* CFU (a cell suspension with an optical density of 1.0 at 550 nm at 1 cm light path) into BHI medium yielded no growth after 36 h at 37° C. in an anaerobic atmosphere.

*C. difficile* toxoid. *C. difficile* culture filtrate was prepared and inactivated as described previously. Briefly, *C. difficile* VPI 10463 was grown in proteose peptone-yeast extract medium for 48 h at 37° C. and inactivated by adding formaldehyde to result in a concentration of 1% (vol/vol) and incubating it at 37° C. for 1 hour. The supernatant was filter sterilized, washed three times with PBS by ultrafiltration (Amicon, 30 KDa), concentrated 10 times in a 500 ml cell concentrator and stored at −20° C. until use.

Animals. Gestating Holstein-Frisian and MRY dairy cows were maintained according to generally accepted dairy management practices in the Netherlands. In experiments described in this communication, mostly Holstein-Frisian cows were employed. Additionally, for a first goat experiment, pregnant goats were selected and maintained in a separate farm, also according to generally accepted management practices. For a second goat experiment pregnant Saanen goats were selected and maintained in a separate farm, also according to generally accepted management practices.

Immunization routes and regimens. Cows: For intramuscular (IM), intra-udder (IUDR) or intra-supramammary lymph node (LMF) immunization, a 2 ml of vaccine preparation in PBS was administered via direct injection into the respective tissues. For intra-nasal (IN) immunization, a 2 ml vaccine preparation was sprayed, while forced to face upwards, into one of the nostrils of cows through a nozzle that was attached to a syringe. For immunizations with the cholera vaccine, DUKORAL was diluted in PBS so that each 2 ml contains $6.5 \times 10^9$ *V cholera* plus 66 μg of CTB. In cases of the *C. difficile* (CD) vaccine, the toxoid and the whole-cell preparations were mixed and diluted in PBS to result in $5 \times 10^{10}$ inactivated *C. difficile* plus 5.5 mg protein of culture supernatant in 2 ml.

First goat experiment: Vaccines that were prepared for cows were further diluted (to 50%) with an equal volume of PBS. For each immunization, 2 ml was used, with the exception of LMF where only one ml was used.

Second goat experiment: Vaccines that were prepared for cows were further diluted (to 50%) with an equal volume of PBS. For each immunization, 2 ml was used, with the exception of LMF where only one ml was used. For intra-nasal (IN) immunization 1 ml vaccine preparation was sprayed into each nostril. The vaccine preparation used for the goats in the second goat experiment was a combination of Dukoral and CD vaccine.

Sample collection and serum and whey preparation. Normally, 5 ml of milk sample from each quarter was collected weekly. When desired, five ml of blood sample was also collected from the tail vein. Whey was prepared from milk samples as described previously. Briefly, fat is removed via centrifugation at 4° C. for 15 min at 4,300×g in a MSE Mistral Centrifuge 6000. Casein is removed by acid precipitation at pH 4.6 by adding sodium acetate and acetic acid followed by centrifugation at room temperature for 15 min at 3,500×g. Blood was left to clot overnight at 4° C. and the serum was obtained by centrifugation.

Assay. Indirect ELISA was carried out to measure immunogen-specific IgG and IgA levels in whey and serum samples. In the beginning (for samples from cows immunized with DUKORAL), ELISA was carried out manually but later (for samples from cows immunized with the CD vaccine and samples from goats immunized with DUKORAL and the CD vaccine), the ELISA robot BioTek OMNI was employed. In both cases, microtiter plates (Greiner 655902, Greiner) were coated with either CTB or inactivated *C. difficile* whole-cell at concentrations of 0.3 μg CTB or $2 \times 10^7$ cells, respectively, per well. Coating was accomplished by incubation for 2 h at 37° C. with CTB or for 2 h at 70° C. with *C. difficile* whole-cell. The plates were washed after each incubation step with PBS containing 0.05% Tween 20. The wells were blocked for 1 h at room temperature with 2% gelatin in PBS. Samples were diluted in PBS in duplicates and were incubated for 1 h at 37° C. For the measurement of antigen-specific bovine antibodies in collected samples, digoxigenin-labelled monoclonal anti-bovine IgA or anti-bovine IgG antibodies were prepared in the lab and were used as the secondary antibodies. For the first goat experiment, for the measurement of antigen-specific goat antibodies in collected samples, monoclonal anti-goat antibodies, instead of anti-bovine antibodies, were employed as the secondary antibodies. For detection, horseradish peroxidase-labelled goat anti-Digoxigenin-POD, Fab fragment (Boehringer Mannheim) was used. ABTS, 2,2'-Azino diethylbenzothiazoline sulfonic acid (Sigma) was used as the substrate for horseradish peroxidase. The optical density, after incubation for 30 min at 37° C., was measured at 415 nm with Bio-Tek $El_x800$ reader. For the second goat experiment, for the measurement of antigen-specific goat antibodies in collected samples, digoxigenin-labelled monoclonal anti-goat IgG antibodies (Sigma) and polyclonal swine anti-goat IgA(Fc) antibodies (Nordic Immunology) were employed as the secondary antibodies. For detection, horseradish peroxidase-labelled goat anti-Digoxigenin-POD, Fab fragment (Boehringer Mannheim) was used, except for the detection of goat IgA antibodies. In this case horseradish peroxidase-labelled rabbit anti-swine IgG (Nordic Immunology) was used as detection antibody. ABTS, 2,2'-Azino diethylbenzothiazoline sulfonic acid (Sigma) was used as the substrate for horseradish peroxidase. The optical density, after incubation for 30 min at 37° C., was measured at 415 nm with Bio-Tek Elx800 reader or Bio-Tek OMNI.

Titers. Levels of immunogen-specifc Ig in samples were expressed in units against the standard of 1000 units/ml. The standard is whey preparation from colostrum of cows that had been immunized with either Dukoral or with the CD vaccine. For the second goat experiment the standard for the goat assays was a whey preparation from colostrum of goats immunized with Dukoral and CD vaccine.

Measurements of total Ig in milk. Total Ig content in each whey sample prepared from immunized and unimmunized milk was measured using high-pressure gel-permeation liquid chromatography.

Results

Generation of standards for antigen-specific antibody assays. Cows in their late pregnancy were immunized four times, with a three-week interval inbetween immunization, before calving. For each immunization, combinations of intra-nasal (IN) and subcutaneous (SC) routes were employed. The immunogen consisted of an equal volume of both vaccines (DUKORAL and the CD vaccine) supplemented with cholera toxin (50 µg/cow/immunization) for the IN route and Freund's incomplete adjuvant (equal volume of the immunogen) for the SC route. From each cow, colostrum of the first milking was collected and whey was prepared. After necessary dilutions (anti-CTB IgA 320×; anti-CTB IgG 8,000×; anti-CD IgA 130×; and anti-CD IgG 8,000×) with PBS, ELISA was performed. The optical density measurements at 415 nm are shown in FIG. 1 (anti-CTB antibodies) and in FIG. 2 (anti-CD antibodies). The whey preparations were pooled and used as standards.

Anti-CTB Ig levels in milk of cows after immunization with the cholera vaccine, Dukoral. With the goal of obtaining high levels of immunogen-specific Ig in the milk of mammals for a sustained period of time, various doses of Dukoral as an antigen were tested in lactating cows using various immunization routes. For example, combinations of subcutaneous (SC), intra-udder (IUDR), intra-supramammary lymph node (LMF), intra-vaginal (IVG) and intra-peritoneal (IP) routes were explored with concentrations of DUKORAL ranging from 50 fold dilution to undiluted ones. Most of the cases, the anti-CTB IgA and IgG titers in the milk were extremely low (FIG. 3 and FIG. 4), when compared to our standard of 1000 units/ml. In a few cases, where the levels reached to a few hundred units, they could not be sustained for much longer than one week. Moreover, the time of appearance of such sporadic peaks was not predictable with respect to the time of immunization.

Anti-CTB Ig levels in milk and blood of cows after nasal spray followed by intra-mammary immunization. A group of six cows in their mature lactation were intra-nasally (IN) immunized once a week for five consecutive weeks with the cholera vaccine, Dukoral. During this five-week period of time, levels of CTB-specific IgA and IgG in whey of the milk and blood were monitored. The low levels (ranging from nil to about 50) in the whey were not significantly different from the results obtained from previous experiments (FIG. 5 and FIG. 6), Anti-CTB IgG levels in the blood, however, continued to increase with repeated IN treatments (starting from about 10 to about 1000 units at the end of the 5 immunization session), whereas CTB-specific IgA in the blood was under the detectable level throughout the experimental period. A single boost treatment, however, brought interesting changes to these results in number of aspects (FIG. 5 and FIG. 6). The boost treatment, which was given 6 weeks after the last IN immunization, consisted of one IM, one IUDR in the rear right quarter, and one LMF also in the rear right quarter, 2 ml each. The measurement of anti-CTB IgA and anti-CTB IgG titers over a five months period is shown in FIG. 5 and FIG. 6. A few conspicuous changes which resulted from the intra-mammary boost immunization are the following: i) Both anti-CTB IgA and anti-CTB IgG responses were observed in all (6/6) animals. ii) In comparison to the titers in the standard (1000 units/ml), IgA responses were very strong, reaching to about 300–500% of the standard levels in some cows. IgG responses were lesser than those of IgA were, but still very high (reaching to 30% of the standard in high responders). iii) IgA responses were significantly longer lasting than those of IgG were. iv) Although there was large variation among animals in immune responses, the immunization method employed here could bring the responses in a synchronous manner among animals. v) IgA responses were more or less limited to the immunized quarters whereas IgG responses generally were spread to all four quarters.

Anti-*C.difficile* (whole-cell) Ig levels in the milk after nasal spray followed by intra-mammary immunization. The interesting observations made in the previous experiment stimulated us to extend the experiment with a different immunogen. Thus, an experiment was carried out with the CD vaccine with a few modifications to the protocol used above. The changes employed in the new protocol were intended for evaluation of the importance of the number of IN immunizations before an intra-mammary injection as well as importance of the interval between IN and intra-mammary immunizations. Each cow in a group of 10 in their mid-lactation received one 2 ml IN and one 2 ml IM immunization. Measurements of anti-CD (whole-cell) IgA and IgG levels in samples collected after the priming, but before the boost, showed expected results: barely detectable (FIG. 7). Three weeks after the priming, each cow received boost treatments, which consisted of one 2 ml IN, one 2 ml IUDR in the rear right quarter, and one 2 ml LMF also in the rear right quarter. Milk samples were continued to be collected weekly and measurements for levels of anti-CD (whole-cell) were made using ELISA. A synchronous surge of immunogen-specific IgG, ranging from 130 to 430 units/ml (against our anti-CD standard of 1000 units/ml) depending on the cow, was observed in the first week after the boost treatments (FIG. 7). As was observed in the case with the cholera vaccine, anti-CD IgG secretion was evenly distributed among the four quarters and the high level secretion was relatively short lived, declining to about 50% levels in less than a two-weeks period. Unlike the immediate IgG responses after the boost, anti-CD IgA responses were slow to appear and could be detected more than a month later (FIG. 8), at which time seven cows (out of 10) were selected out and reimmunized. The reimmunization began with two IN immunizations one week apart. Two weeks thereafter, each cow received boost immunizations of one IN and two LMF immunizations (one for each rear quarter). Unlike in the case of IgG response, and to our surprise, anti-CD IgA response was not synchronized among immunized cows. (Synchrony of anti-CD IgA response could later be restored when combination of LMF and IMA routes was applied as a boost (see the experiment for FIG. 11). Another unexpected result in this experiment is that the strong quarter-specificity, which was observed in the case of anti-CTB IgA response, was no longer observed, i,e. the immunized quarter (rear right) was not necessarily the one which secreated the highest level of anti-CD IgA.

Relative importance of immunization routes. In order to evaluate the relative contribution of each immunization route to the final outcome of antibody secretion in milk, 8 cows were immunized with the CD vaccine. As expected, no anti-CD antibodies were detected in the milk after two-consecutive immunizations via the IN route, two weeks apart from one another (FIG. 9 and FIG. 10). One week after the second IN, all of the cows received the third IN in addition to IMA immunization in the front quarters only (on May 22, 2000). One week thereafter (May 28, 2000), anti-CD IgGs were detectable in all four quarters, but were extremely low (FIG. 9). Anti-CD IgA, however, was not detectable in all four quarters (FIG. 10). The 8 cows then were divided into two groups. Four of them (group 1) received the CD vaccine and the other four (group 2) received saline via the LMF route (on May 29, 2000). One week thereafter, there was a noticeable increase in anti-IgG secretion, only in group 1 implicating that IMA route maybe relatively unimportant to secretion of the IgG class (FIG. 9). As expected, there was no quarter specificity for the secretion. As for the IgA class, however, significant levels of anti-CD antibody secretion were observed in both groups, even in the saline treated group (FIG. 10), although the latter decreased rapidly with a passage of time. The data implies that the LMF route plays the major role for IgA secretion but so does the IMA route to a lesser extent. Again (in addition to the previous experiment), there was an apparent disappearance of quarter specificity. This observation appears independent of routes of immunization and thus must be the result of the vaccine used, i.e., attenuated toxin A of CD, attenuated toxin B of CD and/or inactivated CD cells. The observation is potentially important because it can lead us to a solution to an undesirable logistical problem of having to collect milk from only rear quarters of cows. (Immunization of the front quarters of a cow via the LMF route is not possible without a surgery). The overall levels of anti-CD antibody, both IgA and IgG, in this experiment (FIG. 9 and FIG. 10) were at least an order of magnitude lower than those previously observed. The results clearly indicates that it is highly desirable that boosting via the LMF route acompanies other mucosal route(s) such as IMA, intra-vaginal, intra-rectal and/or preferably intra-nasal. One such example where cows were immunized via the LMF and IMA routes after priming via the IN route is shown in FIG. 11 (anti-CD IgA) and in FIG. 12 (anti-CD IgG).

Levels of total Ig concentration in the milk of immunized cows. Using the methods described in this communication, antigen-specific antibody levels could be reached (close) to the range normally found in the colostrum of immunized cows. Since the total Ig concentration in colostrum of unimmunized cow is approximately two orders of magnitude higher than that in mature milk, an obvious question is what would be the total Ig concentration in the milk of immunized cows. Measurements carried out using high-pressure liquid chromatography showed that total Ig amounts in immunized milk were not significantly different from those in unimmunized milk, which in average was 0.3 mg/ml. The relative amount of total Ig in immunized and unimmunized milk is shown in FIG. 13 (For immune responsiveness of each cow see FIG. 8). The value of the control group is that of a pooled one (of 9 samples).

Immune-responsiveness of other mammals than cows. In order to test applicability of the same immunization method to other mammals for similar results, goats were chosen: they are abundantly available and each can produce up to 2,000 liters of milk. Automatic milking systems also are available and methods of cheese making from their milk, thus whey making, as well as information on their disease status and handling is widely known.

First Goat Experiment:

Ten goats were immunized three times via IN routes, three weeks apart between immunizations. Two weeks after the third IN, each goat received three immunizations one each via IN, IMA and LMF route. Measurements of levels of anti-CTB IgG, anti-CTB IgA, anti-CD IgG and anti-CD IgA in whey samples showed the similar general pattern of the immune response observed in the milk of immunized cows.

Second Goat Experiment:

Generation of standards for antigen-specific antibody assays.

Goats in their late pregnancy were immunized four times, with a three-week interval between immunizations, before birth of the kids. Immunization routes used combined intranasal (IN) and subcutaneous (SC) ways of administration. As immunogen an equal volume of Dukoral and CD vaccine was used supplemented with Diluvac Forte (1:1) (Intervet) for the SC route. Colostrum of the first milking was collected and whey was prepared. ELISA was performed on the samples after dilution with PBS (anti-CTB IgA 100×; anti-CTB IgG 250,000×; anti-CD IgA 50×; anti-CD IgG 16,000×). FIG. 14 (anti-CTB antibodies) and FIG. 15 (anti-CD antibodies) show the optical density measurements at 415 nm. The whey preparations were pooled and used as standards.

Anti-CTB Ig Levels and Anti-CD Ig Levels in Milk after Nasal Spray Followed by Intra-Mammary Immunization.

A group of four goats in their lactation period were intra-nasally (IN) immunized with 2 ml vaccine (a combination of Dukoral and CD vaccine). Two weeks after the first IN, all goats received a second IN immunization. Two weeks after the second IN immunization, each goat received three combined immunizations via IM, IUDR and LMF route. Milk samples were collected during a 12-weeks-period and the immune response (anti-CTB Ig and anti-CD Ig) was monitored by ELISA.

As expected from the results obtained from the same immunizations of the cows, no anti-CTB antibodies and anti-CD antibodies were detected in the milk of the goats after two immunizations via the IN route. Measurements of anti-CTB IgA (FIG. 16) and anti-CTB IgG (FIG. 17) in milk samples collected before the boost treatment showed no detectable levels. The same result was observed for anti-CD (whole cell) IgA (FIG. 18) and IgG levels (FIG. 19). Two weeks after priming, the goats received boost treatments, which consisted of one 2 ml IM, one 2 ml IUDR and one 1 ml LMF. In case of the CD vaccine, an increase of anti-CD IgG levels in the milk was observed in 50% of the goats one week after the boost immunization (FIG. 19). The anti-CD IgG secretion was evenly distributed among the two halves of the udder and the level of secretion was maintained for at least two weeks. Unlike the immediate IgG response, anti-CD IgA (FIG. 18) responses (50% of the goats) were observed at least three weeks after the boost immunization. The anti-CD IgA secretion was also evenly distributed among both halves of the udder. In comparison to the titers anti-CD of the standard (1000 units/ml), immunogen-specific IgA reached 20–25% of the standard levels. In case of the cholera vaccine (Dukoral), an increase of anti-CTB IgG (FIG. 17) levels in milk was observed in 50% of the goats starting from 1–2 weeks after the boost immunization. The anti-CTB IgA (FIG. 16) responses observed in 50% of the goats were slow to appear and could be detected more than a month later. As was observed with the CD vaccine, anti-CTB IgA and IgG secretion in the milk of the immunized goats was evenly distributed in the whole (two halves) udder. In comparison to the titers anti-CTB of the standard (1000 units/ml), immunogen-specific IgA reached >25% of the standard levels.

In conclusion, these results demonstrate that the immunization method used previously in cows is also applicable to other mammals. There is a variation among goats in immune responses, however 50% of the animals showed immunogen-specific Ig levels in the milk after immunization. In all cases the immunogen-specific IgA response is significantly higher than the IgG response. Both anti-CTB IgA and IgG responses observed in goats were significantly higher than anti-CD IgA and IgG responses. The immunogen-specific Ig response in the milk of immunized goats is not restricted to one half of the udder, i.e. the immunized half (right) is not the one that secreted the highest Ig level (not shown). For cows the quarter specificity was observed in case of the anti-CTB IgA response. This dissimilarity can be explained by the different physiology of the udder of cow and goat.

As used herein the term IMA route and IUDR route both refer to intra-udder immunization routes.

BRIEF DESCRIPTION OF THE DRAWINGS

FIG. 1 is a graphic illustration of relative levels of anti-CTB IgA and IgG in colostrum of immunized cows, which were employed as the standard.

FIG. 2 is a graphic illustration of relative levels of anti-CD IgA and IgG in colostrum of immunized cows, which were employed as the standard.

FIG. 3 is a graphic illustration of anti-CTB IgA responses (versus 1,000 units/ml of the standard) in the milk of cows after application of various immunization methods known in the art.

FIG. 4 is a graphic illustration of anti-CTB IgG responses (versus 1,000 units/ml of the standard) in the milk of cows after application of various immunization methods known in the art.

FIG. 5 is a graphic illustration of anti-CTB IgA responses (versus 1,000 units/ml of the standard) in the milk of cows after application of immunization methods of the invention.

FIG. 6 is a graphic illustration of anti-CTB IgG responses (versus 1,000 units/ml of the standard) in the milk of cows after application of immunization methods of the invention.

FIG. 7 is a graphic illustration of anti-CD IgG responses (versus 1,000 units/ml of the standard) in the milk of cows after application of immunization methods of the invention.

FIG. 8 is a graphic illustration of anti-CD IgA responses (versus 1,000 units/ml of the standard) in the milk of cows after application of immunization methods of the invention.

FIG. 9 is a graphic illustration of relative anti-CD IgG responsiveness in milk after various routes of immunization.

FIG. 10 is a graphic illustration of relative anti-CD IgA responsiveness in milk after various routes of immunization.

FIG. 11 is a graphic illustration of anti-CD IgA response (versus 1,000 units/ml of the standard) in milk of cows as the result of boosting via the LMF plus the IMA routes.

FIG. 12 is a graphic illustration of anti-CD IgG response (versus 1,000 units/ml of the standard) in milk of cows as the result of boosting via the LMF plus the IMA routes.

FIG. 13 is a graphic illustration of relative levels of total Igs in the milk of immunized cows compared to those of unimmunized cows.

FIG. 14 is a graphic illustration of relative levels of anti-CTB IgA and IgG in colostrum of immunized goats, which were employed as the standard.

FIG. 15 is a graphic illustration of relative levels of anti-CD IgA and IgG in colostrum of immunized goats, which were employed as the standard.

FIG. 16 is a graphic illustration of anti-CTB IgA responses (versus 1,000 units/ml of the standard) in the milk of immunized goats after application of immunization methods of the invention.

FIG. 17 is a graphic illustration of anti-CTB IgG responses (versus 1,000 units/ml of the standard) in the milk of immunized goats after application of immunization methods of the invention.

FIG. 18 is a graphic illustration of anti-CD IgA responses (versus 1,000 units/ml of the standard) in the milk of immunized goats after application of immunization methods of the invention.

FIG. 19 is a graphic illustration of anti-CD IgG responses (versus 1,000 units/ml of the standard) in the milk of immunized goats after application of immunization methods of the invention.

What is claimed is:

1. A method of making a harvested mammary secretion product comprising an antibody specific for an antigens, the method comprising:
   hyperimmunizing a farm-animal for the antigen (i) via a mucosal passage of the farm-animal, the mucosal passage selected from the group consisting of an intravaginal passage, an intrarectal passage, and an intranasal passage of the animal, or (ii) via inhalation through an airway of the farm animal;
   administering the antigen to a mammary gland and/or a supramammary lymph node of the farm-animal; and
   harvesting the mammary secretion product from the farm-animal.

2. The method of claim 1, wherein the hyperimmunizing step comprises administering the antigen via inhalation through an airway of the farm-animal.

3. The method of claim 2, wherein the hyperimmunizing step comprises administering the antigen intranasally to the farm-animal.

4. The method of claim 1, wherein the mammary secretion product is milk.

5. The method of claim 1, wherein the antibody is an IgA antibody.

6. The method of claim 1, further comprising boosting an immune response to the antigen in the farm-animal.

7. The method of claim 6, wherein the boosting step comprises administering the antigen to an airway, a mammary gland, and/or a supramammary lymph node of the farm-animal.

8. A method of making an antibody composition comprising an antibody specific for an antigen, the method comprising:
   hyperimmunizing a farm-animal for the antigen (i) via a mucosal passage of the farm-animal, the mucosal passage selected from the group consisting of an intravaginal passage, an intrarectal passage, and an intranasal passage of the animal, or (ii) via inhalation through an airway of the farm animal;
   administering the antigen to a mammary gland anti/or a supramammary lymph node of the farm-animal;
   harvesting the mammary secretion product from the farm-animal; and
   deriving the antibody composition from the harvested mammary secretion product.

9. A method of making an antigen-specific antibody, the method comprising:
   hyperimmunizing a farm-animal for the antigen (i) via a mucosal passage of the farm-animal, the mucosal passage selected from the group consisting of an intravaginal passage, an intrarectal passage, and an intranasal passage of the animal, or (ii) via inhalation through an airway of the farm animal;
   administering the antigen to a mammary gland and/or a supramammary lymph node of the farm-animal;
   harvesting a mammary secretion product from the farm-animal; and
   deriving the antigen-specific antibody from the harvested mammary secretion product.

10. A method of making a medicament comprising an antibody specific for an antigen, the method comprising:
  hyperimmunizing a farm-animal for the antigen (i) via a mucosal passage of the farm-animal, the mucosal passage selected from the group consisting of an intravaginal passage, an intrarectal passage, and an intranasal passage of the animal, or (ii) via inhalation through an airway of the farm animal;
  administering the antigen to a mammary gland and/or a supramammary lymph node of the farm-animal;
  harvesting the mammary secretion product from the farm-animal; and
  preparing the medicament from the secretion product.

11. A method of making a food product comprising an antibody specific for an antigen, the method comprising:
  hyperimmunizing a farm-animal for the antigen (i) via a mucosal passage of the farm-animal, the mucosal passage selected from the group consisting of an intravaginal passage, an intrarectal passage, and an intranasal passage of the animal, or (ii) via inhalation through an airway of the farm animal;
  administering the antigen to a mammary gland and/or a supramammary lymph node of the farm-animal;
  harvesting the mammary secretion product from the farm-animal; and
  preparing the food product from the secretion product.

12. The method of claim 1, wherein the antigen is administered at least once in the supramammary lymph node.

13. The method of claim 1, wherein the antigen is administered at least twice in the supramammary lymph node.

14. The method of claim 1, wherein the farm-animal is a cow or a goat.

15. The method of claim 1, wherein the hyperimmunizing step further comprises administering an adjuvant to the farm-animal.

16. The method of claim 15, wherein the adjuvant is toxin B of *Clostridium difficile*.

17. The method of claim 1, wherein the antigen is derived from a culture of *Clostridium difficile*.

18. The method of claim 17, wherein the antigen is a protein from a *Clostridium difficile* (VPI10463) cell.

19. The method of claim 17, wherein the antigen is a *Clostridium difficile* spore.

20. The method of claim 19, wherein the antigen comprises *Clostridium difficile* Toxin A.

21. The method of claim 17, wherein the antigen comprises *Clostridium difficile* Toxin B.

22. The method of claim 17, wherein the antibody is specific for a protein of *Clostridium difficile*.

23. The method of claim 17, wherein the antibody is specific for a *Clostridium difficile* spore.

24. The method of claim 1, wherein the farm-animal is a lactating farm-animal.

25. The method of claim 1, wherein the airway administration is achieved in the form of aerosols.

26. The method of claim 1, wherein the hyperimmunizing step comprises at least two airway administrations of the antigen.

27. The method of claim 1, wherein the hyperimmunizing step comprises at least four airway administrations of the antigen.

28. The method of claim 1, wherein the antigen is administered to the mammary gland and/or supramammary lymph node of the farm-animal about 6 weeks following the hyperimmunizing step.

29. The method of claim 1, wherein the harvested mammary secretion product has an IgA titer of at least 1000 units/ml.

30. The method of claim 1, wherein the harvested mammary secretion product has an IgA titer of at least 1000 units/ml and is harvested up to about 10 weeks after the antigen is administered to the mammary gland and/or the supramammary lymph node of the farm-animal.

31. The method of claim 1, wherein the harvested mammary secretion product has an IgG titer of at least 100 units/ml.

32. The method of claim 1, wherein the harvested mammary secretion product has an IgG titer of at least 100 units/ml and is harvested up to about 8 weeks after the antigen is administered to the mammary gland and/or the supramammary lymph node of the farm-animal.

33. The method of claim 1, wherein the hyperimmunizing step further comprises administering the antigen intramuscularly to the farm animal.

34. The method of claim 1, wherein the antigen is administered to the mammary gland and/or supramammary lymph node of the farm-animal about 3 weeks following the hyperimmunizing step.

35. The method of claim 1, wherein the harvested mammary secretion product has an IgG titer of about 130 units/ml to about 430 units/ml.

36. The method of claim 1, wherein a second hyperimmunization step is performed after the antigen is administered to the mammary gland and/or supramammary lymph node of the farm-animal.

37. The method of claim 36, wherein the antigen is administered a second time to the mammary gland and/or supramammary lymph node of the farm-animal following the second hyperimmunization step.

38. The method of claim 37, wherein the mammary secretion product harvested after the second mammary gland and/or supramammary lymph node administration has an IgG titer of at least 400 units/ml.

39. The method of claim 37, wherein the mammary secretion product harvested after the second mammary gland and/or supramammary lymph node administration has an IgA titer of at least 3500 units/ml.

40. The method of claim 37, wherein the mammary secretion product harvested after the second mammary gland and/or supramammary lymph node administration does not have a strong quarter specificity for IgA titer.

41. The method of claim 4, wherein the milk from the farm-animal comprises at least 0.5 g/ml of antibody specific for the antigen.

42. The method of claim 4, wherein the milk from the farm-animal comprises at least 15 g/ml of antibody specific for the antigen.

43. The method of claim 4, wherein the milk from the farm-animal comprises at least 50 g/ml of antibody specific for the antigen.

44. The method of claim 4, wherein the milk from the farm-animal comprises the antibody specific for the antigen in a quantity of at least 50 percent of the average quantity of the antibody specific for the antigen that is obtainable from a colostrum of the farm-animal.

45. The method of claim 4, wherein the milk from the farm-animal comprises the antibody specific for the antigen in a quantity of at least 100 percent of the average quantity of the antibody specific for the antigen that is obtainable from a colostrum of the farm-animal.

46. The method of claim 4, wherein the milk from the farm-animal comprises the antibody specific for the antigen in a quantity of at least 200 percent of the average quantity of the antibody specific for the antigen that is obtainable from a colostrum of the farm-animal.

47. The method of claim 40, wherein the antibody specific for the antigen is an IgA antibody.

48. The method of claim 41, wherein the antibody specific for the antigen is an IgA antibody.

49. The method of claim 42, wherein the antibody specific for the antigen is an IgA antibody.

50. The method of claim 43, wherein the antibody specific for the antigen is an IgA antibody.

51. The method of claim 44, wherein the antibody specific for the antigen is an IgA antibody.

52. The method of claim 45, wherein the antibody specific for the antigen is an IgA antibody.

53. The method of claim 1, further comprising removing fat and casein from the harvested mammary secretion product.

54. The method of claim 8, further comprising removing fat and casein from the harvested mammary secretion product.

55. The method of claim 9, further comprising removing fat and casein from the harvested mammary secretion product.

56. The method of claim 10, further comprising removing fat and casein from the harvested mammary secretion product.

57. The method of claim 11, further comprising removing fat and casein from the harvested mammary secretion product.

* * * * *